US012748067B2

(12) United States Patent
Kornbluth et al.

(10) Patent No.: US 12,748,067 B2
(45) Date of Patent: Sep. 29, 2026

(54) NANOELECTRONIC DEVICE

(71) Applicant: Robert Bosch GmbH, Stuttgart (DE)

(72) Inventors: Mordechai Kornbluth, Brighton, MA (US); Yu Jin, Chicago, IL (US); Christopher Johnson, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 187 days.

(21) Appl. No.: 18/390,654

(22) Filed: Dec. 20, 2023

(65) Prior Publication Data

US 2025/0208085 A1 Jun. 26, 2025

(51) Int. Cl.
*G01N 27/327* (2006.01)
*C12Q 1/6869* (2018.01)
*G01N 33/487* (2006.01)

(52) U.S. Cl.
CPC ....... *G01N 27/3278* (2013.01); *C12Q 1/6869* (2013.01); *G01N 33/48721* (2013.01)

(58) Field of Classification Search
CPC ......... G01N 27/3278; G01N 33/48721; C12Q 1/6869
See application file for complete search history.

(56) References Cited

U.S. PATENT DOCUMENTS 10,175,190 B2 1/2019 Tayebi et al.
11,187,672 B2 11/2021 Afzali-Ardakani et al.
11,345,987 B2 5/2022 Cheng et al.
11,391,730 B2 7/2022 Kornbluth et al.
2010/0040935 A1* 2/2010 Babes-Dornea ...... H01M 4/921 429/494
2016/0245774 A1* 8/2016 Tayebi ............... G01N 27/3278
2019/0169684 A1 6/2019 Oldham et al.
2019/0376925 A1 12/2019 Choi et al.
2020/0080958 A1* 3/2020 Yang .................... G01N 27/407
2021/0288152 A1 9/2021 Reddy Arava et al.

OTHER PUBLICATIONS

B.L. Hanssen, Recent strategies to minimise fouling in electrochemical detection systems, Rev Anal Chem 2016, 35(1), pp. 1-28 (Year: 2016).*

Tijjani Adam et al., "Recent advances in techniques for fabrication and characterization of nanogap biosensors: A review," Wiley, Biotechnol Appl. Biochem. 2022;69:1395-1417.

Simon Batzner et al., "E(3)-equivariant graph neutral networks for data-efficient and accurate interatomic potentials," Nature Communications, https://doi.org/10.1038/s41467-022-29939-5, www.nature.com/naturecommunications.

(Continued)

*Primary Examiner* — C. Sun
(74) *Attorney, Agent, or Firm* — BROOKS KUSHMAN P.C.

(57) ABSTRACT

A nanoelectronic device includes first and second nano electrodes, a nanogap defined by the first and second nano electrodes and separating the first and second nano electrodes, a solvent present in the nanogap and including a plurality of redox molecules, and a component configured as a disruptor of solvent atomic structures, the component forming a surface portion on a bulk portion within the device, the component being located at a predetermined distance away from the first and second nano electrodes.

19 Claims, 3 Drawing Sheets

(56) References Cited

OTHER PUBLICATIONS

Bozana Colovic et al., "Wetting properties of titanium oxides, oxynitrides and nitrides obtained by DC and pulsed magnetron sputtering and cathodic arc evaporation," Materials Science-Poland, 37(2), 2019, pp. 173-181, http://www.materialsscience.pwr.wroc.pl/ DOI: 10.2478/msp-2019-0031.
Ryan J. White et al., "Electrochemistry in Nanometer-Wide Electrochemical Cells," Langmuir 2008, 24, 2850-2855.
John F. Smalley et al., "The Kinetics of Electron Transfer through Ferrocene-Terminated Alkanethiol Monolayers on Gold," J. Phys. Chem. 1995, 99, 13141-13149.
Benjamin L. Hanssen et al., "Abstract," Simultaneous Programming of Two Parameters in Micro- and Capillary-HPLC, vol. 35, No. 1, Apr. 1, 20216, pp. 1-28.
International Search Report and Written Opinion dated Feb. 26, 2025 received in related PCT Appln. No. PCT/IB2024/062927, filed Dec. 12, 2024.
International Preliminary Report on Patentability & Written Opinion dated Jun. 20, 2026 which issued in related PCT Application No. PCT/IB2024/062927.

* cited by examiner

NANOELECTRONIC DEVICE

TECHNICAL FIELD

The present disclosure relates to a nanoelectronic device such as a nanogap sensing device with improved redox molecule transport, its architecture and chemical composition, and a method of making and using the same.

BACKGROUND

With advancing tools and methods, nanoscale manufacturing is gaining traction. Yet, the science and engineering of structures, devices, and systems made of atoms on the nanoscale requires new material approaches such that the desired nano structures may be formed and function in a desired way.

SUMMARY

In one or more embodiments, a nanoelectronic device is disclosed. The device may include first and second nano electrodes, a nanogap defined by the first and second nano electrodes and separating the first and second nano electrodes, a solvent present in the nanogap and including a plurality of redox molecules, and a component configured as a disruptor of solvent atomic structures, the component forming a surface portion on a bulk portion within the device, the component being located at a predetermined distance away from the first and second nano electrodes. The predetermined distance may be about 0.5 to 10 nm away from at least one of the first and second nano electrodes. The surface portion may be hydrophobic. The bulk portion may include a dielectric material. The surface portion may include a halogen. The surface portion may have a first porosity and the bulk portion may have a second porosity, the first porosity being greater than the second porosity. The bulk portion may include Pt. The device may be a DNA sequencing device.

In another embodiment, a nanoelectronic system is disclosed. The system may include a substrate supporting first and second nano conductors separated by a nanogap, a solvent including redox molecules present in the nanogap, and a disruptor of solvent atomic structures. The disruptor may be spaced apart from the first and second nano conductors such that there is about 0.5 to 10 nm between at least the first nano conductor and the disruptor. The disruptor may be a hydrophobic structure. The disruptor may form a surface portion on the substrate. The nanoelectronic system may also have current collectors connected to the first and second nano conductors, and the disruptor may form a surface portion of the current collectors. The disruptor may be hydrophobic. The disruptor may have a first porosity and the substrate may have a second porosity, the first porosity being greater than the second porosity.

In yet another embodiment, a nanoelectronic biosensor is disclosed. The biosensor may include a substrate supporting first and second nano electrodes, a nano gap separating the first and second nano electrodes and including a solvent with redox molecules and atomic interfacial structures, and a hydrophobic component configured to disrupt the atomic interfacial structures, the component located at a predetermined distance from the electrodes. The predetermined distance may be about 0.5 to 10 nm. The hydrophobic component may form a top layer on the substrate. The hydrophobic component may have a first porosity and the substrate may have a second porosity, the first porosity being greater than the second porosity. The hydrophobic component's distance to the first and second nano electrodes may be equal. The hydrophobic component may extend an entire length of the nanogap except for 0.5-10 nm from each one of the first and second nano electrodes.

DETAILED DESCRIPTION

Figure 1:
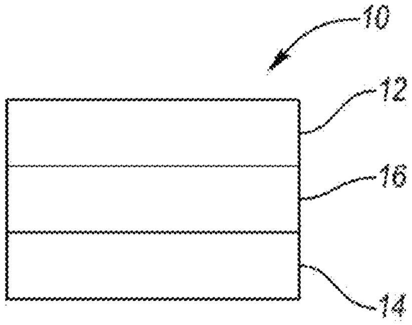
FIG. 1 is a schematic depiction of a non-limiting example nanoscale device current collectors sandwiching a dielectric.

Embodiments of the present disclosure are described herein. It is to be understood, however, that the disclosed embodiments are merely examples and other embodiments may take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present embodiments. As those of ordinary skill in the art will understand, various features illustrated and described with reference to any one of the figures may be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Except in the examples, or where otherwise expressly indicated, all numerical quantities in this description indicating amounts of material or conditions of reaction and/or use are to be understood as modified by the word "about" in describing the broadest scope of the disclosure. Practice within the numerical limits stated is generally preferred. Also, unless expressly stated to the contrary: percent, "parts of," and ratio values are by weight; the description of a group or class of materials as suitable or preferred for a given purpose in connection with the disclosure implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "substantially," "generally," or "about" means that the amount or value in question may be the specific value designated or some other value in its neighborhood. Generally, the term "about" denoting a certain value is intended to denote a range within ±5% of the value. As one example, the phrase "about 100" denotes a range of 100±5, i.e. the range from 95 to 105. Generally, when the term "about" is used, it can be expected that similar results or effects according to the disclosure can be obtained within a range of ±5% of the indicated value. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, and reaction conditions (e.g., pressure, pH, flow rates, etc.) can be practiced with plus or minus 50 percent of the values indicated rounded to or truncated to two significant figures of the value provided in the examples. In a refinement, concentrations, temperature, and reaction conditions (e.g., pressure, pH, flow rates, etc.) can be practiced with plus or minus 30 percent of the values indicated rounded to or truncated to two significant figures of the value provided in the examples. In another refinement, concentrations, temperature, and reaction conditions (e.g., pressure, pH, flow rates, etc.) can be practiced with plus or minus 10 percent of the values indicated rounded to or truncated to two significant figures of the value provided in the examples.

For all compounds expressed as an empirical chemical formula with a plurality of letters and numeric subscripts (e.g., $CH_2O$), values of the subscripts can be plus or minus 50 percent of the values indicated rounded to or truncated to two significant figures. For example, if $CH_2O$ is indicated, a compound of formula $C_{(0.8-1.2)}H_{(1.6-2.4)}O_{(0.8-1.2)}$. In a refinement, values of the subscripts can be plus or minus 30 percent of the values indicated rounded to or truncated to two significant figures. In still another refinement, values of the subscripts can be plus or minus 20 percent of the values indicated rounded to or truncated to two significant figures.

As used herein, the term "and/or" means that either all or only one of the elements of said group may be present. For example, "A and/or B" means "only A, or only B, or both A and B". In the case of "only A," the term also covers the possibility that B is absent, i.e. "only A, but not B".

It is also to be understood that this disclosure is not limited to the specific embodiments and methods described below, as specific components and/or conditions may, of course, vary. Furthermore, the terminology used herein is used only for the purpose of describing particular embodiments of the present disclosure and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" as a subset.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description, and does not necessarily preclude chemical interactions among constituents of the mixture once mixed. First definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

In the past, manufacturing was focused on dimensions visible with the naked eye. Nowadays, new tools, systems, and solutions are enabling manufacturing at much smaller scales such as nanoscale. Nanomanufacturing is a set of industrial processes based on nanotechnology, where products are developed at the nanoscale. Nanotechnology is the science and engineering of structures, devices, and systems made of atoms arranged on the 1 to 100 nm length scale. While in the past, manufacturing was influenced by nanoscale—such as defects or advantageous structures on the nanoscale of materials—their presence was not controlled.

Recently, nanotechnology use cases have been applied in various sectors, from medicine and information technology to transportation, food, retail, and others. In the world of electronics, non-limiting example technologies which are being shrunk to the nanoscale include quantum sensors, quantum dots, nanoelectromechanical systems (NEMS), semiconductor memory, and biomolecule sensors, molecular circuits, transistors (field-effect transistors), nanodiodes, photovoltaic cells, and photonic antennas, etc.

Electronic nanoscale devices typically include two current collectors (CC) that sandwich a dielectric whose width is in the order of about 10 nm (about 3 to 100 nm). The dielectric prevents current transfer from the first CC to the second CC, as shown chemically in FIG. 1. In FIG. 1, the device 10 includes CC 12 and 14, and dielectric 16. The current typically transfers in some other way, e.g. through a sensing molecule, through a quantum dot, through a semiconductor logic gate, etc.

Figure 2:
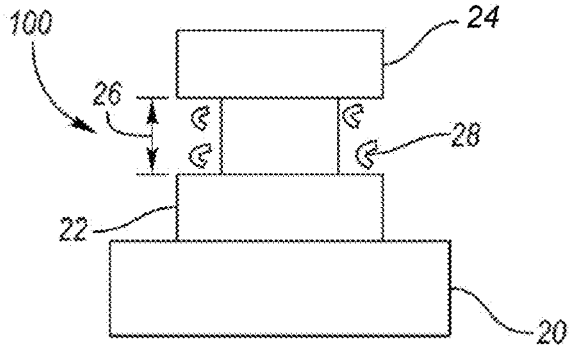
FIG. 2 is a schematic depiction of a non-limiting example nanoscale biosensing device with biomolecules to be detected.

Some sensor technologies such as biosensors include a nanogap electrode device. Electrical nanogap devices for biosensing are useful to detect relatively small quantities of biomolecules. A nanogap biosensor includes two electrodes separated by typically no more than about 300 nm. The nanogap biosensor is used to electrically detect biologically relevant materials, reactions, or interactions in a solution. A non-limiting example of such a device is schematically shown in FIG. 2. The depicted nanogap capacitive biosensor 100 includes a substrate 20, a bottom electrode 22, a top electrode 24, the two electrodes 22 and 24 are separated by a nanogap 26. 28 denotes biomolecules to be detected within the nanogap 28 by the biosensor 100.

Figure 3:
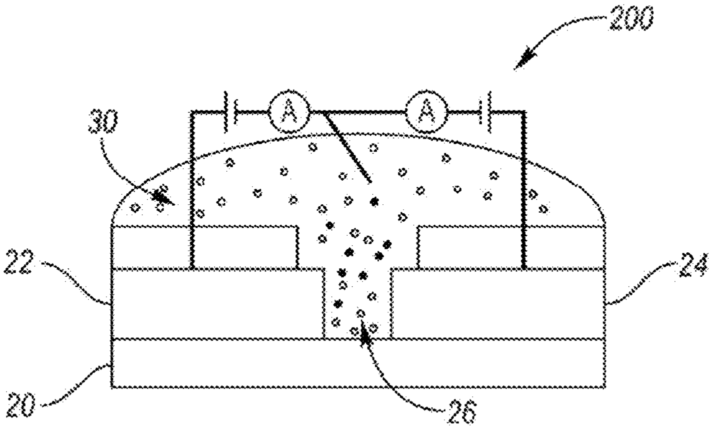
FIG. 3 is a schematic depiction of another non-limiting example nanoscale biosensing device.

A schematic non-limiting example of another nanogap electrode device is shown in FIG. 3. The device 200 of FIG. 3 includes a substrate 20, two electrodes 22 and 24 separated by a nanogap 26. The example of FIG. 3 also shows dissolved molecules 30 present in the nanogap 26 between the electrodes 22, 24.

Sometimes the sensing mechanism includes small molecules such as redox molecules which undergo electron transfer to/from the electrode. The nanogap may trap the redox species and allow the redox species to repeatedly cycle between the electrodes (redox cycling). The redox cycling may lead to an enhanced electrochemical signal. The redox molecules may be attached to other molecules such as nucleotides that are part of a DNA sequence.

While strides have been made in improving sensing on the nanoscale, it would be desirable to further develop the sensing systems and methods such as increasing their stability, reliability, and sensing capability. For example, it would be desirable to increase the level of current which may be measured between the electrodes.

In one or more embodiments, a nano device is disclosed. Nano or nanoscale refers to dimensions between about 1-100 nm. The nano device may be a mechanism, unit, cell, or part of a nano system. The nano device may be a nanoelectronic device, nanoelectric device, nano sensing device, a nano biosensor, or a combination thereof. Sensing may relate to bio sensing, DNA sequencing, etc. The device may include a nanometer-scale detection region (nano gap) which is interrogated using electrical components described herein to measure the presence or activity of a biomolecule. The device may rely solely on the measurement of currents, voltages, or both to detect binding of the biomolecule. For example, the device may have direct transduction of biomolecules' specific binding into electrical signals such as resistance, impedance, capacitance, dielectric, or field effect.

The device may be a planar nanogap device, where both nano electrodes or nano conductors face each other horizontally, or a vertical nanogap device. At least one nano electrode may include Pt, Au, indium tin oxide (ITO), iridium oxide, or another material.

The device may include a substrate. The substrate may be supporting a first nano electrode or conductor, a second nano electrode or conductor, a dielectric material, one or more additional components, or a combination thereof. The substrate may be a metal substrate. The substrate may have a metal bulk region. The substrate may be in contact with the nanogap. The first and second nano electrodes are separated by the nanometer gap or nanogap. The nanogap may measure about 1-25, 5-22, or 12-20 nm. The nanogap may measure about 1, 2, 3, 4, 5, 6, 7, 8, 9, 10, 11, 12, 13, 14, 15, 16, 17, 18, 19, 20, 21, 22, 23, 24, or 25 nm. Any range of the numerals named herein is contemplated. Other dimensions of the nanogap within the nanoscale are contemplated.

The nanogap may include a dielectric or a polarizable material with low or substantially no electrical conductivity. The system further includes an electrical circuit connecting the electrodes. The electrodes are structured to transfer electrons to, from, or through the solvated molecules discussed below, thus creating a current that is measurable.

The device may include a solvent such as water. Other solvents are contemplated. The solvent may include one or more or a plurality of substructures or atomic structures such as interfacial water structures or hydration layers separated by interlayer distance(s). The device may further include a plurality of solvated molecules present in the nano gap or detection region. The solvated molecules may be redox molecules subjected to redox cycling within the device. The redox molecules may include ferrocene, methylene blue, phenothiazine, or BODIPY dyes, the like, or a combination thereof.

The device may operate in the following manner. Nanosized biomolecules may be trapped in the nanogap or the detection region between the electrodes of the device. The biomolecules may be detected by observing/recognizing their electrical behavior (resistance/impedance, capacitance/dielectric, or field-effect) within the nanogap. For example, a strand of reference DNA may be positioned within a nanogap of the device disclosed herein. A voltage may be then applied across the nanogap, and a measurement of the capacitance may be taken. The capacitance may be determined by the dielectric property of the material in the nanogap, which undergoes changes as a result of hybridization. Alternatively, as was mentioned above, presence of the target molecule may be detected by observation of conducting changes, or other electrical behavior.

Figure 4:
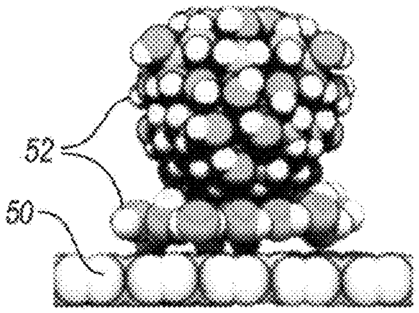
FIG. 4 shows a 3D model of water structures present in water at a water-metal interface.

It was discovered via the simulations discussed in the Experimental Section that the redox mobility is typically limited by the structure of the water layers adjacent the electrodes. Water, or another solvent, includes molecules and/or ions which have intermolecular or ion interactions with each other and other materials surrounding the water or solvent. As a result, formation of various atomic structures within the water or solvent may influence interactions with other atoms. For example, on some surfaces, water may form interfacial water structures such as hydration layers separated by an interlayer distance which may differ based on the type of interface. Interfacial water structures may be thus present in the bulk water within the nanogap. A non-limiting example of interfacial water structures within the bulk water adjacent a surface is shown in FIG. 4. A surface 50 is a metal surface, 52 denotes water structures occurring on the interface. The water structures such as those depicted in FIG. 4 may be present in a typical nanogap, form obstacles or steric hinderances, and thus restrict redox mobility.

The restricted mobility of the redox molecules further limits the current measurable between electrodes of traditional biosensing devices which negatively affects their sensitivity and detection abilities. Thus, in contrast, the device disclosed herein further includes a structure or component arranged to avoid, tune, eliminate, minimize, or alter water structuring and thus increase electron current detectable in the nanogap.

The device component disclosed herein is configured to prevent solvent structuring adjacent to the electrode, thereby allowing the redox molecules to move closer to the electrode surface(s). In other words, the component disclosed herein is configured to prevent, avoid, modify, adjust, eliminate, minimize, or a combination thereof, water or solvent atomic structures within the water or solvent. The prevention, avoidance, adjustment, elimination, or minimization may be focused on the area of the nanogap in the vicinity of the electrodes, dielectric, or both. The vicinity may be adjacent, immediately adjacent the electrodes, spatially distanced from the electrodes, or a combination thereof. The component is thus a disruptor, remover, or minimizer of undesirable atomic interfacial water structures or hydration layers.

The component disclosed herein may be a surface portion forming a coating or layer(s) on the bulk region. The bulk region may be a substrate, a dielectric, an electrode material, or another surface within the nanogap. The structure may be thus present on the electrode, the substrate, the dielectric, or a combination thereof. The structure may be present in a nanojunction or connection of nanoscale components named herein.

In at least one embodiment, the component is not present on the electrodes, but rather is spatially removed from the electrodes such that the electrodes are free of the component. As such, the component is located at a predetermined distance from at least one of the electrodes or both electrodes. The predetermined distance may be equal for both electrodes such that the placement of the component is symmetrical within the nanogap. The surface portion may be provided on the dielectric, the substrate, or another non-electrode portion of the nanogap. The surface portion may be located at about 0.5-10, 1-9, or 2-8 nm from one, both, or all nano electrodes. The structure may be located at about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.00 nm from one or more nano electrodes. The predetermined distance may be about 0.5-10, 1-9, or 2-8 nm from the first, second, or both electrode(s). Presence of the surface portion may increase redox molecule mobility within the nanogap by altering any present water structures, layering, or both, removing the steric hinderance caused by the water structures, increasing the ability of redox molecules to move within the nanogap, or a combination thereof.

The surface portion may form islands, continuous layer, discontinuous layer, or a combination thereof. The surface portion may form a pattern or be irregular. The surface portion may extend the entire length or a portion of a bulk portion. The portion may be an entire length of the nanogap except for the 0.5-10 nm from each of the nano electrodes. For example, a portion of the current collector bulk may include the surface portion. For example, the surface portion may form a top layer of the dielectric, extend an entire or partial length of the dielectric, or both. In another example, the nano electrodes are free of the surface portion, but the surface portion is present on a bulk portion located about 0.5-10 nm from the electrode(s). The component may be a self-supporting component or surface portion adjacent to or spatially removed from the electrode(s), as was described above.

The surface portion may have a greater roughness, hydrophobicity, or both than the bulk region and or other areas of the device. The surface portion has a first roughness, the bulk region has a second roughness. The first roughness is greater than the second roughness. Roughness relates to the quality of a surface of not being smooth, it relates to the spatial variability structure of surfaces. Roughness includes one or more peaks, valleys, protrusions, spikes, waves, vertical deviations from the nominal surface, or a combination thereof. A surface with greater roughness may include a greater number of pores or increased porosity than a smooth surface. The surface portion may thus have a first porosity, the bulk portion may have a second porosity. The second porosity is smaller than the first porosity; the first porosity is greater than the second porosity.

Hydrophobicity relates to the physical property of a molecule seemingly repelled from a mass of water. It is the opposite of hydrophilicity. Hydrophobicity may be influenced by several surface parameters such as surface energy and texture. Typically, hydrophobic substances include non-polar molecules that repel water and attract neutral molecules and non-polar solvents. The surface portion may be hydrophobic while the bulk portion may be hydrophilic or less hydrophobic than the surface portion.

The increased roughness and/or hydrophobicity may break up the undesirable water structures in the nanogap. The surface portion may be formed by slightly corroding the bulk portion of the electrode to remove atoms such as Pt atoms. Alternatively, extra material may be deposited onto the bulk portion of the electrode to form a hydrophobic surface or an undulating surface, peaks, valleys, protrusions, spikes, increased porosity, etc., or a combination thereof. The deposition may include atomic layer deposition, providing a gas to reduce the oxygen portion, resulting in a surface with increased porosity.

The surface portion may include one or more components, compounds, or materials rendering the surface portion hydrophobic, including but not limited to halogens such as fluorine or chlorine, specifically PtF moieties, PtCl moieties, $TiNO_x$, a ceramic such as a $Si_xC_yO_z$ ceramic, silicon, silicon oxide, silicone dioxide, or a combination thereof.

In at least one embodiment, during operation of the device, an AC voltage may be applied to the electrodes, thereby oscillating the water molecules. The oscillation may raise the temperature, thereby increasing diffusion and electron transfer and also disrupting the solvent structuring. Alternatively, an infrared optical field, microwave generator, piezoelectric generator, or electroactive polymer may be used.

In another embodiment, at least some of the molecules may include a hydrophilic moiety such as —OH terminations to break up the solvent structure and allow it to get closer to the electrode surface and move away at will.

It is contemplated that various strategies of breaking up unwanted water structures may be used individually or in a combination within the device disclosed herein or in a system including the device. As a result, the electron transfer between the electrode(s) and redox molecule(s) in the water or another solution is enhanced.

Figure 5:
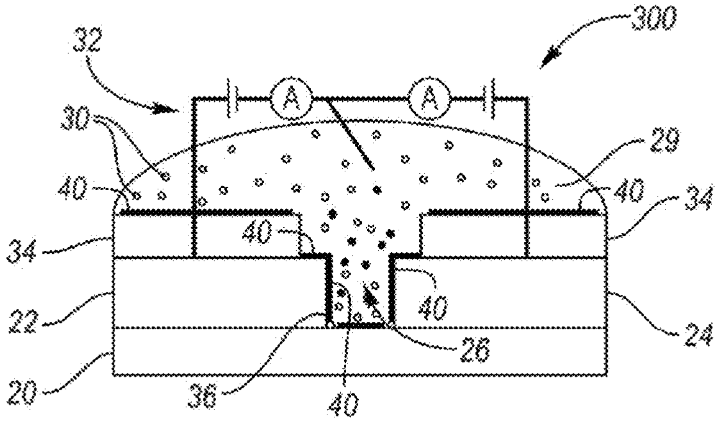
FIG. 5 is a schematic depiction of a non-limiting example sensing device disclosed herein.

A non-limiting example of a nanoelectronic device disclosed herein is shown in FIG. 5. The nanoelectronic device 300 is a sensing device including a substrate 20 and first and second nano electrodes 22, 24 separated by a nanogap 26. The device 300 also shows a solvent 29 with dissolved/solvated redox molecules 30 present in the nanogap 26 between the electrodes 22, 24. The device also includes an electrical circuit 32 and current collectors 34 adjacent the electrodes 22, 24. The device includes a component 40 configured to minimize presence of water structures negatively influencing the redox molecule transfer in the nanogap. The component 40 may be provided in one or more locations within the device. While FIG. 5 identifies several locations for placement of the component 40, any of these locations alone may be sufficient. Presence of the component 40 within one or more of the depicted locations is contemplated. For example, the component may be provided on a dielectric 36, on the current collector(s) 34, on the substrate 20, on the electrode 22, electrode 24, or a combination thereof. In at least some embodiments, at least one of the electrodes 22 and 24 is free of the component 40, is not in contact with the component 40, or both. Both electrodes 22, 24 may be free of the component, surface portion 40.

A method of increasing sensing capability of a sensing device is disclosed herein. The method may include enhancing electron transfer between the electrode(s) and solvated molecule(s) in the water or solution within the nanogap. The method may include increasing current measurable within the nanogap. The method may include redox molecule transport within the nanogap. The method may include disrupting, adjusting, minimizing, eliminating, reducing, etc. one or more water structures of the solution within the nanogap, in the vicinity of the electrodes, dielectric, substrate, another surface, or a combination thereof. By disrupting the water structures, the redox molecules are able to move adjacent to the electrode(s) which in turn increases the current measurable in the nanogap.

The method may include providing a hydrophobic surface portion on a bulk region. The method may include forming a hydrophobic surface portion on an electrode, adjacent the electrode, spatially distancing the hydrophobic coating from the electrode within a distance described above such as about, at least about, or at most about 1-10, 2-9, or 3-8 nm from an electrode, or a combination thereof. The method may include adding a hydrophobic or superhydrophobic material, compound, or composition to form the surface portion.

The method may include providing a surface portion on a bulk region, the surface portion having an increased roughness, porosity, surface fluctuations, undulations, or formations in comparison to the bulk region or other portions of the device. The method may include coating a bulk portion with a hydrophobic material, corroding the bulk portion, removing atoms from the bulk portion, adding atoms to the bulk portion, etching the bulk portion. The method may include depositing material by atomic layer deposition, sputtering, etc.

Experimental Section

A simulation was designed to identify obstacles negatively affecting the redox cycling, specifically redox mobility within the nanogap. Limitations of the redox mobility impose limits on the current that can be measured between the electrodes separated by the nanogap. By identifying conditions affecting the redox mobility, and correcting them, the limits on the measurable current may be removed or altered.

A simulation model was built to model the redox transfer of ferrocene (Fc) in a nanojunction using first-principle methods. The electron transfer rate $k_{ox}$ and $k_{red}$ was computed using Marcus theory and fitted to a simple exponential as shown in FIG. 6, with the parameters $$k_0 = 3.85 \times 10^{8^\circ}\ \mathrm{s}^{-1},\ \beta = 2.072\ \text{Å}^{-1},\ z_0 = 4^\circ\ \text{Å}.$$

Figure 6:
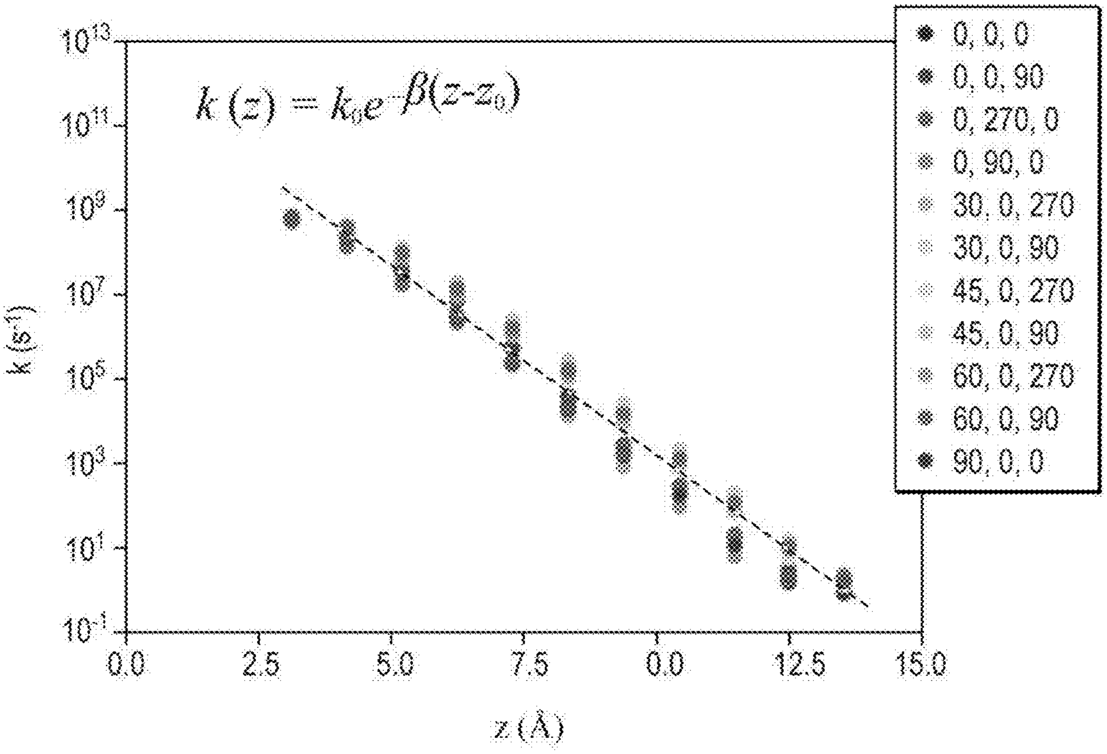
FIG. 6 is a plot of electron transfer rate of ferrocene (Fc) as a function of distance from a Pt electrode.

In FIG. 6, the electron transfer rate of Fc is depicted as a function of distance from a Pt electrode. The different shades of gray are varied angular orientations of the Fc molecule. The points fit on a master exponential curve shown in the dotted line, with the parameters above. The effect with an overpotential η is adjusted by multiplying with a Butler-Volmer factor of $$e^{\frac{\eta}{2k_BT}}$$

for the reduction reaction and $$e^{\frac{\eta}{2k_BT}}$$

for the oxidization reaction. The resulting outcome was that it is desirable to have the redox molecules as close to the electrode as possible for redox behavior.

The finding was incorporated into a model including a Monte-Carlo simulation for electron transfer between Fc and two electrodes and a Markov process for the diffusion of Fc in a nanojunction separated by 3 nm. The probability of an electron transfer was computed using the exponential above, whereas the diffusion was assumed to follow a 1-dimensional random walk with step length and step time commensurate with the temperature at 300 K, i.e. average thermal velocity of about 25 meV and diffusion coefficient of about $10^{-9}\ \mathrm{m^2 s^{-1}}$. If the random walk is unbiased, i.e. all distances from the electrode have an equal probability of occupation, the total current is computed as shown in FIG. 7.

Figure 7:
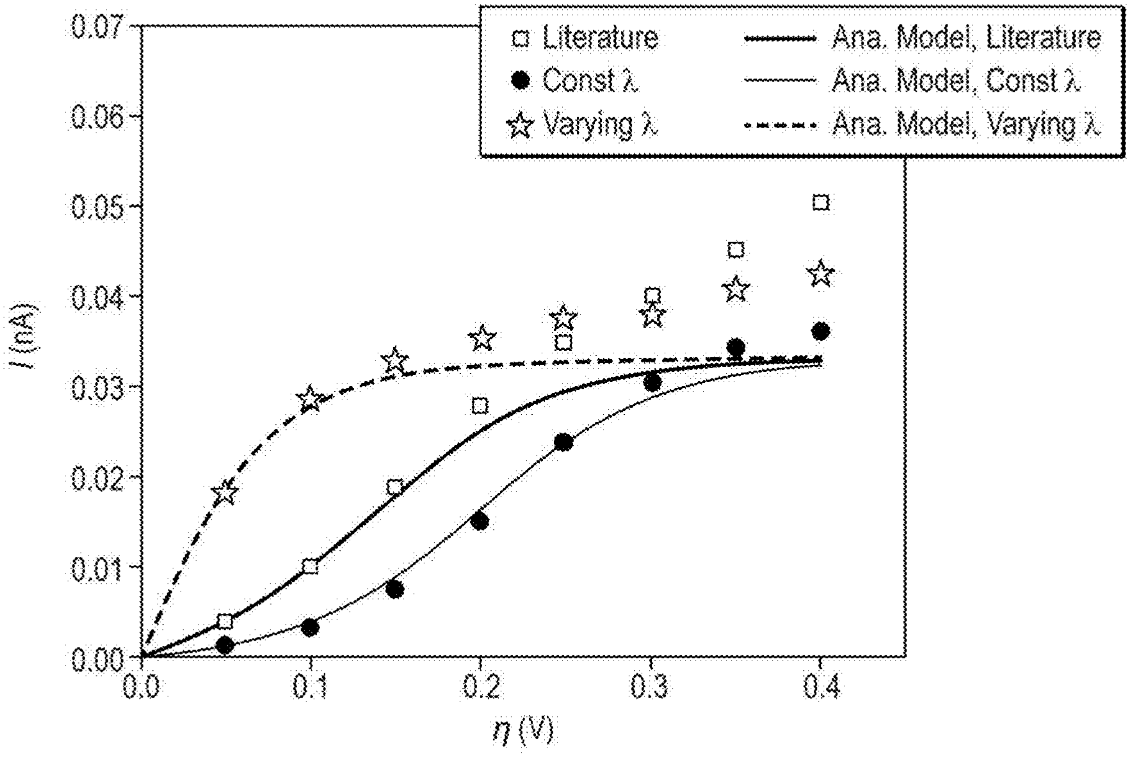
FIG. 7 is a plot of electrical current as a function of overpotential.

FIG. 7 is a plot of the current as a function of overpotential. The current for a 3 nm nanogap at different overpotential (η) is shown. The overpotential on the left (right) electrode is set to η (−η). The squares, dots, and stars represent results computed using the exponential expression of electron transfer rate with different sets of parameters (see Table 1 below). The Butler-Volmer analytical limit is shown in dashed lines; it can be seen that the approximation breaks down for high overpotential because the electron transfer can happen farther from the surfaces of the nanogap.

TABLE 1

Computation of current as a function of overpotential

| | Description | $k_0$ ($s^{-1}$) | β (Å$^{-1}$) |
|---|---|---|---|
| Literature | [ref: Smalley et al., 10.1021/j100035a016] | ~6 × $10^8$ | ~1 |
| Const λ | Current disclosure. Constant solvent reorganization energy λ. | 3.85 × $10^8$ | 2.072 |
| Varying λ | Current disclosure. Considering the distance dependence of the solvent reorganization energy λ. | 2.30 × $10^{10}$ | 2.441 |

Yet, the simple random walk does not strictly represent the diffusion behavior because Fc has a preferential distance adjacent to the electrode. For a Pt electrode, this was modeled using a NequIP machine-learning potential including Pt, Fc, and water. The resulting potential of mean force (PMF) shows a strong preference for Fc to occupy a distance ~4 Å from the electrode, with a barrier of ~0.35 eV to move away from there.

Figure 8A:
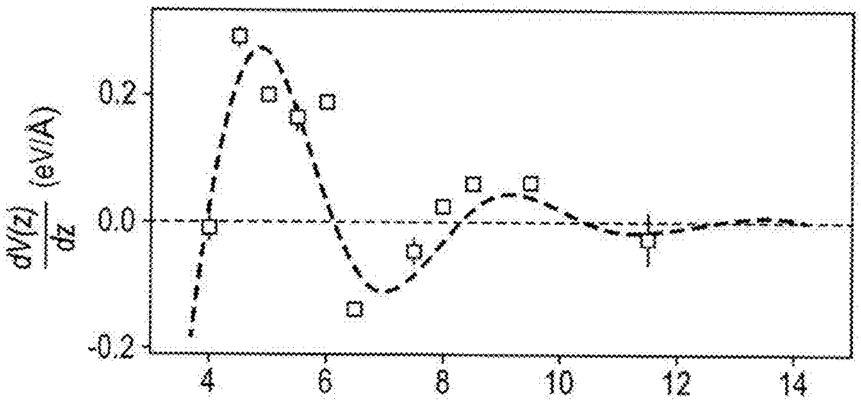
FIGS. 8A and 8B are plots showing molecule diffusion behavior within the nanogap.

FIG. 8A shows an analysis of the force exhibited on molecules at a particular distance to the electrode. The squares are calculated points, the dashed line is an analytical fit to it. The flat portions of the graph indicate a low force due to large distance from the electrode.

Figure 8B:
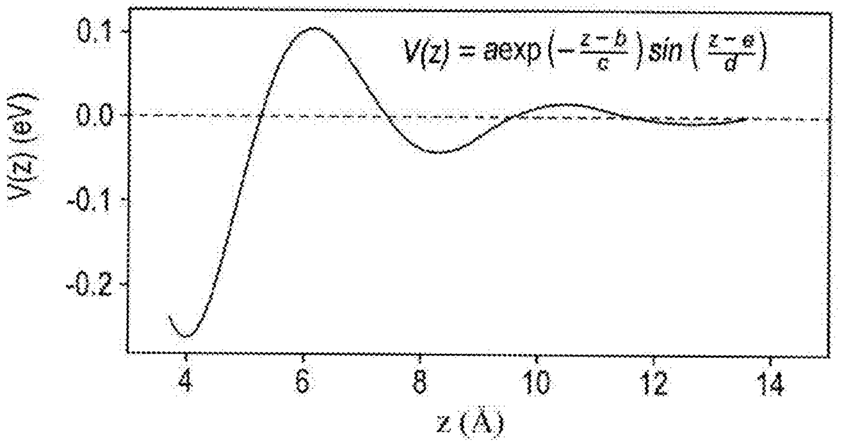

Potential of mean force (PMF) obtained by fitting the average force acting on the Fc molecule in the z direction in water at fixed distances from the electrode (squares in FIG. 8A) with the derivative of the analytical potential V(z) is shown in FIG. 8B. The fitted derivative is shown in dashed line in FIG. 8A and the corresponding potential V(z) is shown in dashed line in the FIG. 8B.

Figure 9:
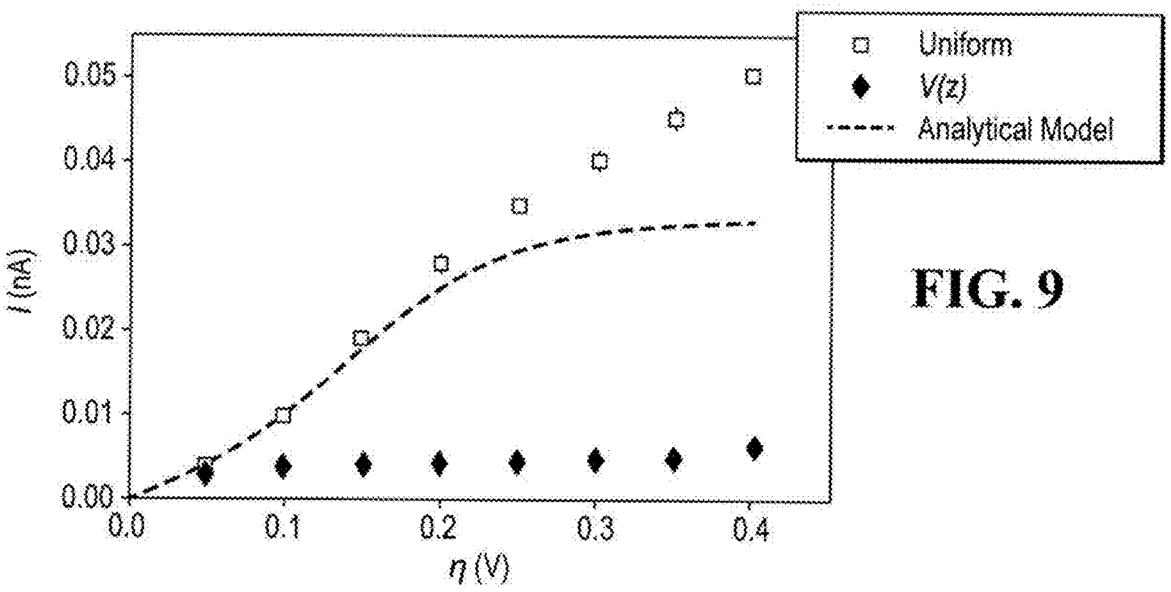
FIG. 9 is a plot of electrical current as a function of overpotential from simulations disclosed herein versus Butler-Volmer analytical model versus solvent structuring and the potential $V_{(z)}$.

When the PMF V(z) of FIG. 8B and the associated non-uniform distribution was included in the simulation of 1D diffusion by a Markov process, the current dropped drastically, as can be seen in FIG. 9. The current from simulations with simple random walk accounting for the uniform distribution of Fc (squares in FIG. 9) exceeds the Butler-Volmer analytical model at high overpotential. However, when solvent structuring and the potential V(z) is taken into account (rhombus), the current drops because the Fc is trapped adjacent to the electrode.

The trapping of the redox molecule should be thus remedied by disrupting the obstacles present in the solvent in the nanogap. The disrupting may be conducted at a predetermined distance from the electrodes such as the nanojunction adjacent the electrodes (about 0.5-10 nm). Removing the obstacles in the solvent may increase mobility of the redox molecules and remove or reduce limits on the measurable current in the nanogap.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A nanoelectronic device comprising:

first and second nano electrodes;

a nanogap defined by the first and second nano electrodes and separating the first and second nano electrodes;

a solvent present in the nanogap and including a plurality of redox molecules; and a component configured as a disruptor of solvent atomic structures, the component forming a surface portion on a substrate within the nanogap between the first and second nano electrodes and being spaced apart from and not in contact with the first and second nano electrodes, the first and second nano electrodes being free of the component, the surface portion comprising a hydrophobic termination configured to disrupt the solvent atomic structures at the surface of the component in contact with the solvent.

2. The nanoelectronic device of claim 1, wherein a distance between the component and at least one of the first and second nano electrodes is about 0.5 to 10 nm.

3. The nanoelectronic device of claim 1, wherein the substrate includes a dielectric material.

4. The nanoelectronic device of claim 1, wherein the surface portion includes a halogen.

5. The nanoelectronic device of claim 1, wherein the surface portion has a first porosity and the substrate has a second porosity, the first porosity being greater than the second porosity.

6. The nanoelectronic device of claim 1, wherein the substrate includes Pt.

7. The nanoelectronic device of claim 1, wherein the device is a DNA sequencing device.

8. A nanoelectronic system comprising:

a substrate supporting first and second nano conductors separated by a nanogap;

a solvent including redox molecules present in the nanogap; and a disruptor of solvent atomic structures, the disruptor being disposed on the substrate within the nanogap between the first and second nano conductors and being physically separated from and not in contact with the first and second nano conductors, the first and second nanoconductors being free of the disruptor.

9. The nanoelectronic system of claim 8, wherein the disruptor is a hydrophobic structure.

10. The nanoelectronic system of claim 8, wherein the disruptor forms a surface portion on the substrate.

11. The nanoelectronic system of claim 8, wherein the disruptor extends across at least a portion of the nanogap and terminates short of each of the first and second nano conductors.

12. The nanoelectronic system of claim 8, wherein the disruptor is hydrophobic.

13. The nanoelectronic system of claim 8, wherein the disruptor has a first porosity and the substrate has a second porosity, the first porosity being greater than the second porosity.

14. A nanoelectronic biosensor comprising:

a substrate supporting first and second nano electrodes;

a nano gap separating the first and second nano electrodes and including a solvent with redox molecules and atomic interfacial structures; and a hydrophobic component configured to disrupt the atomic interfacial structures, the component disposed on the substrate and extending across at least a portion of the nanogap between the first and second nano electrodes and being physically separated from and not in contact with the first and second nano electrodes, the component terminating short of each of the first and second nano electrodes such that a gap is maintained between the component and each electrode.

15. The nanoelectronic biosensor of claim 14, wherein a distance between the component and at least one of the first and second nano electrodes is about 0.5 to 10 nm.

16. The nanoelectronic biosensor of claim 14, wherein the hydrophobic component forms a top layer on the substrate.

17. The nanoelectronic biosensor of claim 14, wherein the hydrophobic component has a first porosity and the substrate has a second porosity, the first porosity being greater than the second porosity.

18. The nanoelectronic biosensor of claim 14, wherein the hydrophobic component's distance to the first and second nano electrodes is equal.

19. The nanoelectronic biosensor of claim 14, wherein the hydrophobic component extends an entire length of the nanogap except for 0.5-10 nm from each one of the first and second nano electrodes.

* * * * *